United States Patent
Nakamura

(10) Patent No.: US 7,628,490 B2
(45) Date of Patent: Dec. 8, 2009

(54) SLIT LAMP MICROSCOPE AND OPHTHALMIC LASER TREATMENT APPARATUS WITH THE MICROSCOPE

(75) Inventor: Hirokazu Nakamura, Nishio (JP)

(73) Assignee: Nidek Co., Ltd., Gamagori (JP)

( * ) Notice: Subject to any disclaimer, the term of this patent is extended or adjusted under 35 U.S.C. 154(b) by 93 days.

(21) Appl. No.: 11/902,617

(22) Filed: Sep. 24, 2007

(65) Prior Publication Data

US 2008/0079901 A1 Apr. 3, 2008

(30) Foreign Application Priority Data

Sep. 29, 2006 (JP) .............................. 2006-268677

(51) Int. Cl.
*A61B 3/10* (2006.01)
(52) U.S. Cl. ...................... 351/214; 351/221
(58) Field of Classification Search ................. 351/214, 351/215, 221, 205, 246, 200; 359/368, 372–380
See application file for complete search history.

(56) References Cited

U.S. PATENT DOCUMENTS

| | | | |
|---|---|---|---|
| 4,396,260 A | 8/1983 | Takizawa et al. | |
| 4,838,671 A | 6/1989 | Papritz et al. | |
| 5,311,224 A | * 5/1994 | Enomoto | 351/214 |
| 5,321,446 A | * 6/1994 | Massig et al. | 351/214 |
| 5,342,351 A | 8/1994 | Blaha et al. | |
| 2005/0237486 A1 | 10/2005 | Su et al. | |
| 2006/0176447 A1 | 8/2006 | Reis | |

FOREIGN PATENT DOCUMENTS

| | | |
|---|---|---|
| DE | 928 205 | 6/1963 |
| DE | 42 05 865 A1 | 9/1993 |
| DE | 42 27 390 A1 | 2/1994 |
| DE | 10 2005 032 501 A1 | 3/2006 |
| EP | 1 486 160 A2 | 12/2004 |
| JP | A-62-269923 | 11/1987 |
| JP | A-2002-224036 | 8/2002 |

* cited by examiner

*Primary Examiner*—Hung X Dang
(74) *Attorney, Agent, or Firm*—Oliff & Berridge, PLC

(57) ABSTRACT

A binocular slit lamp microscope for observing a patient's eye, comprises: an objective lens; binocular eyepieces; and a mechanism that includes a plurality of optical systems and is arranged to switch the optical systems to be selectively placed in a predetermined position between the objective lens and the binocular eyepieces on an observation optical path, the mechanism including a variable magnification optical system for changing observation magnification and a viewing angle changing optical system for changing a viewing angle between a right viewing path and a left viewing path.

4 Claims, 7 Drawing Sheets

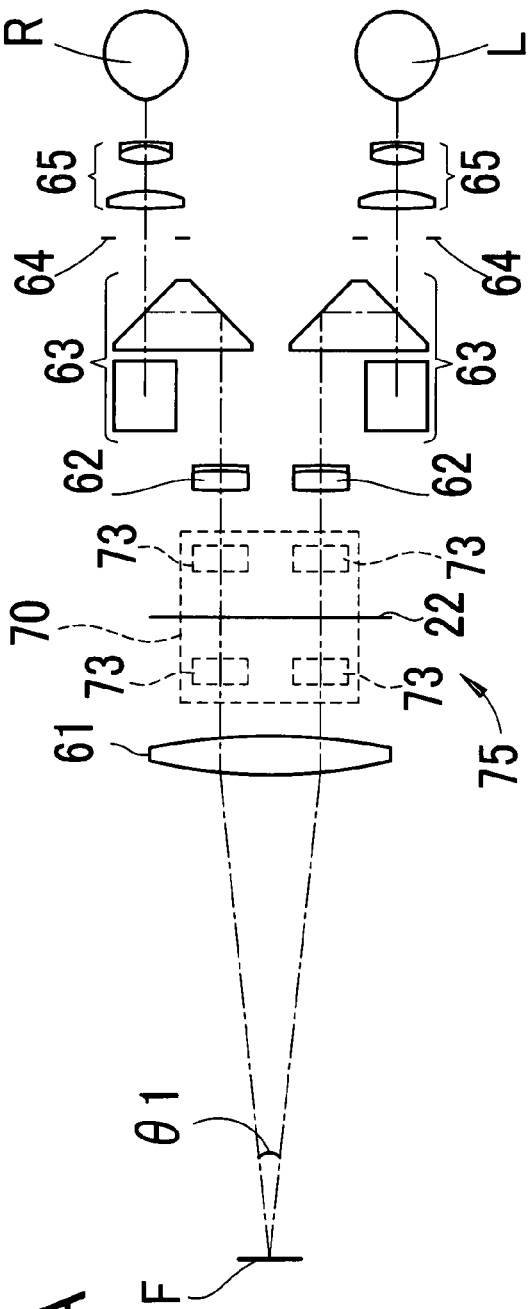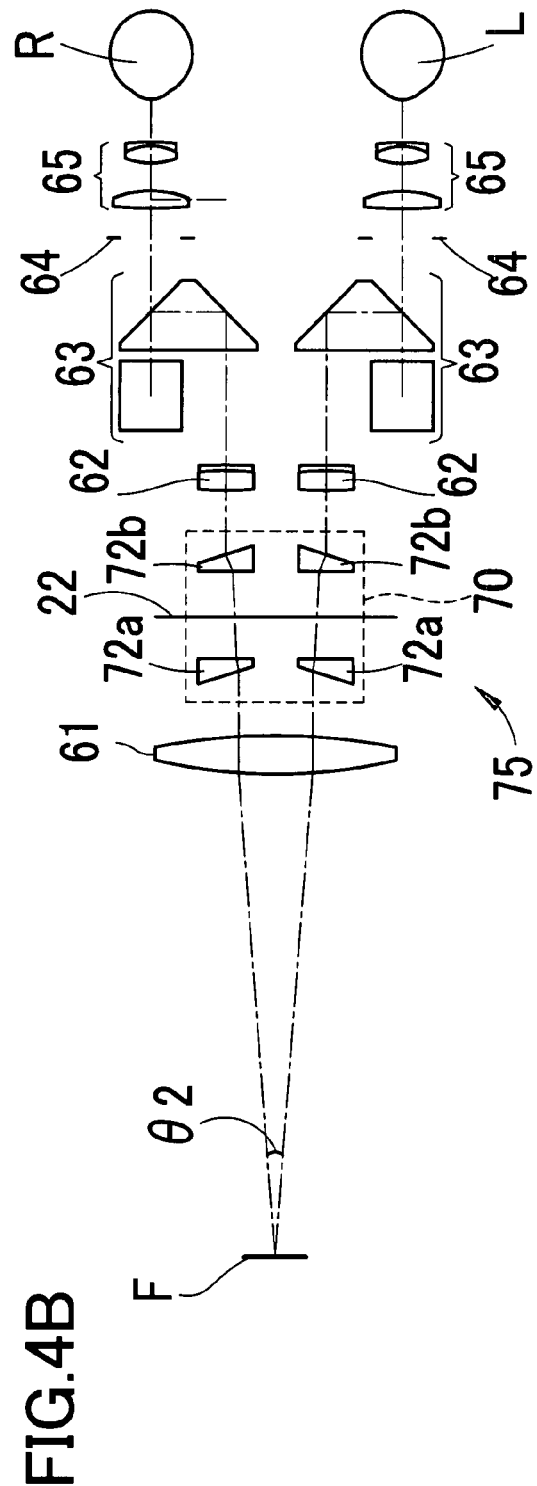

SLIT LAMP MICROSCOPE AND OPHTHALMIC LASER TREATMENT APPARATUS WITH THE MICROSCOPE

BACKGROUND OF THE INVENTION

1. Field of the Invention

The present invention relates to a slit lamp microscope for observing a patient's eye (an examinee's eye) while irradiating a treatment laser beam to the patient's eye, and an ophthalmic laser treatment apparatus provided with the slit lamp microscope.

2. Description of Related Art

In an ophthalmic laser treatment apparatus arranged to irradiate a treatment laser beam (a laser beam for photocoagulation) to a patient's eye, particularly, a fundus of the eye, a binocular slit lamp microscope is used for observation. As such a slit lamp microscope, there is a configuration that comprises a variable magnification mechanism including a rotating drum with a variable magnification optical system placed within a binocular observation optical system for changing observation magnification (power) by rotating the rotating drum (see for example JP2002-224036A, hereinafter referred to as "Patent document 1"). Besides, there is also a configuration in which an optical element called Stereo-Variator for changing a viewing angle is installed between an objective lens and a variable magnification mechanism in order to adjust a binocular field of view during observation (see for example U.S. Pat. No. 4,838,671 (JP62-269923 (1987)A), hereinafter referred to as "Patent document 2").

In the apparatus of Patent document 2, however, a mechanical part of the stereo-variator is about 70 mm in length, resulting in an increased length of an observation optical system. Accordingly, the microscope has an extended working distance (herein, corresponding to a distance from eyepieces for observer (operator) to a patient's eye). In the photocoagulation laser treatment of a fundus of the patient's eye, an operator holds a contact lens on the patient's eye with hand and simultaneously performs laser irradiation using illumination light and treatment light delivered to the patient's eye. If the working distance is long, therefore, some operators who have short arms may not stably hold the contact lens in contact with a patient's eye while observing the patient's eye. Further, the mechanical part of the stereo-variator in Patent document 2 is large in size and needs a rotating mechanism for largely changing the viewing angle, leading to a high cost.

BRIEF SUMMARY OF THE INVENTION

The present invention has an object to provide a slit lamp microscope with a mechanism for changing an observation viewing angle while restraining extension of a working distance and providing an advantage in cost, and a an ophthalmic laser treatment apparatus provided with the slit lamp.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose, one aspect of the invention provides a binocular slit lamp microscope for observing a patient's eye, comprising: an objective lens; binocular eyepieces; and a mechanism that includes a plurality of optical systems and is arranged to switch the optical systems to be selectively placed in a predetermined position between the objective lens and the binocular eyepieces on an observation optical path, the mechanism including a variable magnification optical system for changing observation magnification and a viewing angle changing optical system for changing a viewing angle between a right viewing path and a left viewing path.

According to another aspect, the invention provides an ophthalmic laser treatment apparatus comprising a treatment laser source and an irradiation optical system for irradiating a laser beam emitted from the laser source to the patient's eye, wherein the aforementioned slit lamp microscope is used as an observation unit for observing the patient's eye.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIGS. 4A and 4B are schematic diagrams to explain an observation viewing angle;

DETAILED DESCRIPTION OF THE PREFERRED EMBODIMENTS

Figure 1:
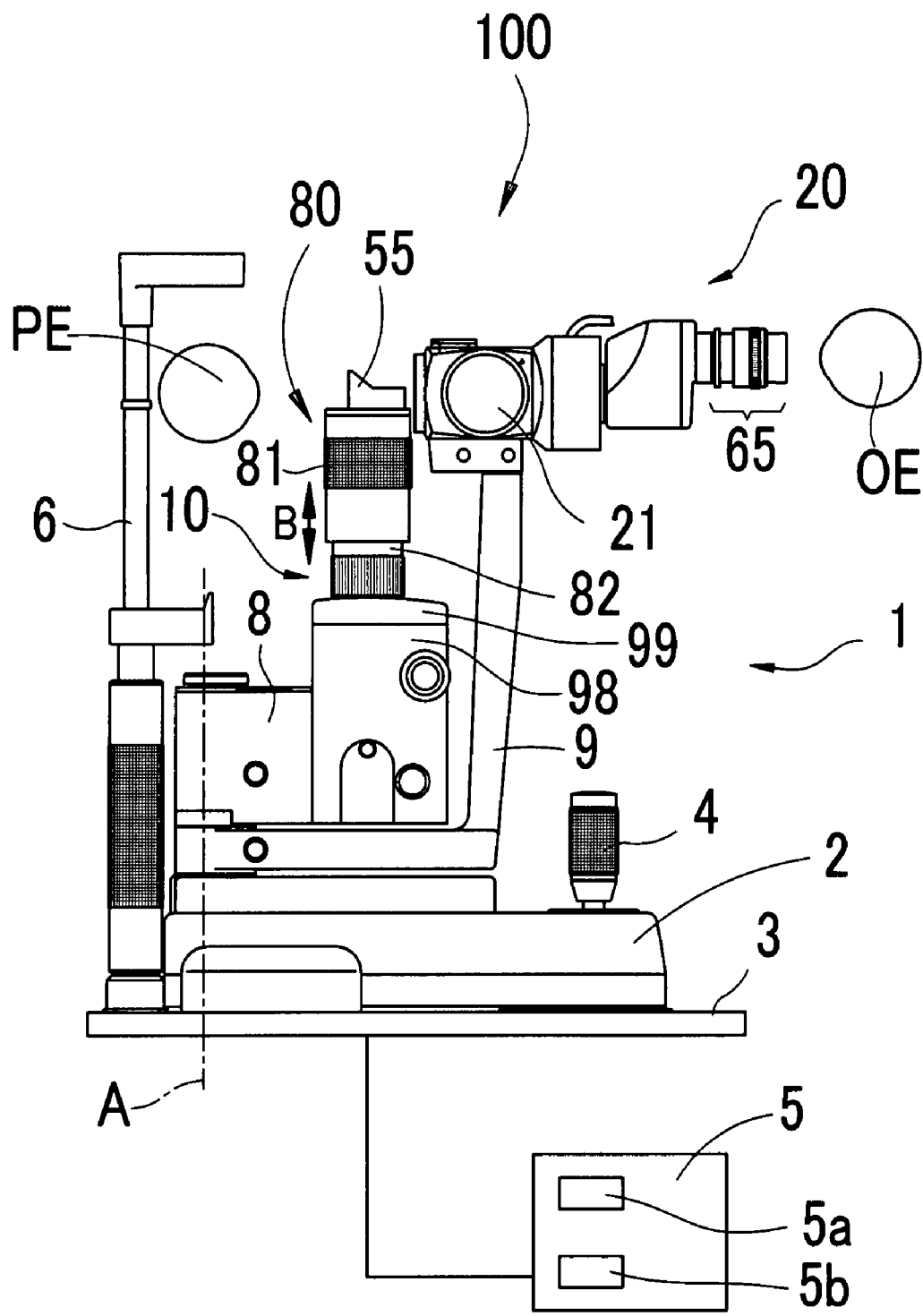
FIG. 1 is a side view of an ophthalmic laser treatment apparatus including a slit lamp and others of a preferred embodiment.
Figure 2:
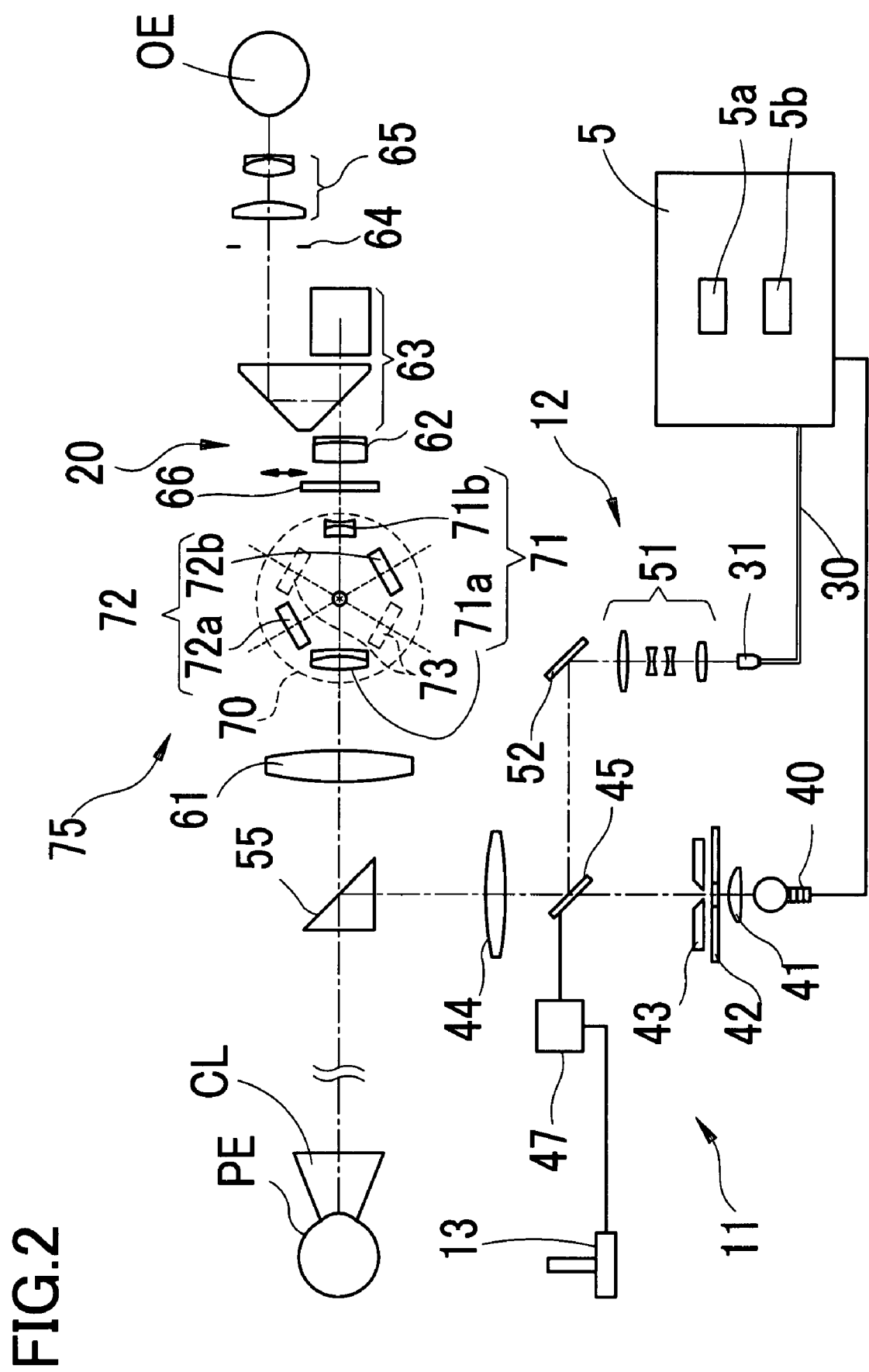
FIG. 2 is a schematic diagram showing a configuration of the ophthalmic laser treatment apparatus.

A detailed description of a preferred embodiment of the present invention will now be given referring to the accompanying drawings. FIG. 1 is a side view of a slit lamp and an ophthalmic laser treatment apparatus provided with the slit lamp in the present embodiment. FIG. 2 is a schematic diagram showing a configuration of the ophthalmic laser treatment apparatus.

In the present embodiment, the ophthalmic laser treatment apparatus 100 is a photocoagulation apparatus. The slit lamp 1 is used for observation or others of a patient's eye PE. The slit lamp 1 has a base 2 as a lower part, which is mounted on a table 3. Further, the base 2 is movable in a horizontal direction relative to the table 3 by operation of a joystick 4. An operator (an observer) can roughly and finely move the base 2 relative to the table 3 by operating the joystick 4. A headrest 6 having a chinrest, a forehead rest, and others is attached to the table 3 for supporting the head of the patient in a stationary state.

A main box 5 includes a treatment laser source 5a, an aiming laser source 5b for generating an aiming beam, and an optical system for delivering those laser beams. The main box 5 is further provided with various switches for setting conditions of the laser beams to be irradiated such as energy power and irradiation time.

A light projecting unit 10 is arranged to irradiate an illumination beam and laser beams to the patient's eye PE. This light projecting unit 10 includes a cylindrical housing in which optical elements, light sources, and others are housed, which is attached to a base unit 8. The light projecting unit 10 comprises an illumination section 11 including an illumination optical system for illuminating the patient's eye PE and a laser delivery optical system 12 for delivering the treatment laser beam to the eye PE. The illumination section 11 includes various kinds of optical parts. A mirror 52 is placed somewhere in an illumination optical axis of the illumination section 11 to combine waveforms of the laser beams. The mirror 52 is aligned with the laser delivery optical system 12. In a head section 80 of the light projecting unit 10, a prism mirror 55 is placed for delivering the illumination light and the laser beams to the patient's eye PE. One end of a laser delivery fiber 30 is aligned with the laser delivery optical system 12. The other end of the fiber 30 is connected to the main box 5. The fiber 30 serves to deliver the treatment laser beam and the aiming beam emitted from the main box 5 to the laser delivery optical system 12. The head section 80 is vertically movable as indicated by an arrow B in FIG. 1. The head section 80 further includes a tilting mechanism for tilting the optical axes of the illumination light and the laser beams by tilting the prism mirror 55 (the details thereof will be described later). This tilting mechanism allows the optical paths of the illumination light and the laser beams to be shifted while keeping forming positions of the illumination light and the laser beams unchanged. The head section 80 is mounted on a base part 99 which is fixed to a lamp housing 98 constituting the light projecting unit 10. When the observer rotates a first outer sleeve 81 of the head section 80 with hand, the head section 80 can be moved upward/downward. The base unit 8 to which the light projecting unit 10 is fixed is rotatable about an axis A relative to the base 2. Thus, the observer can arbitrarily change projecting angles of the illumination light and the laser beams as needed.

A microscope 20 is a binocular microscope enabling stereoscopic (binocular) observation of a part to be observed through predetermined viewing paths. This microscope 20 is fixed to an arm 9. The operator can change observation magnification by rotating a switching knob (a switching device) 21 and further change the angle between right and left viewing paths (hereinafter, a binocular viewing angle), the details thereof will be described later. Every time the knob 21 is turned about 60°, a click mechanism (which is not shown) makes the operator feel a click so that the operator recognizes the switching of the observation magnification and the observation viewing angle.

As in the case of the light projecting unit 10, the arm 9 to which the microscope 20 is fixed is rotatable about the axis A relative to the base 2. The operator therefore can arbitrarily change an observation angle of the microscope 20.

Next, an internal configuration of the slit lamp 1 will be explained referring to FIG. 2. In the illumination section 11 of the light projecting unit 10, an illumination light source 40 is placed. Visible light emitted from the illumination light source 40 passes through a condenser lens 41 and then a variable aperture 42 whereby the height of the light is defined. The light then passes through a variable slit plate 43 whereby the width of the light is defined and the light is formed into a slit shape. After passing through the variable slit plate 43, the illumination light passes through a projection lens 44 and is reflected by the prism mirror 55 to illuminate the patient's eye PE. When a fundus of the eye PE is to be observed, the above illumination and observation may be conducted through a contact lens CL. The illumination section 11 includes a waveform-combining mirror 45. This mirror 45 makes the laser beams from the laser delivery optical system 12 coaxial with the illumination light. The mirror 45 is connected to a manipulator unit 47 for two-dimensionally changing the inclination of the mirror 45 within a range of several angles. The manipulator unit 47 is connected to an operation unit 13 to be operated by the operator. Based on signals from the operation unit 13, the manipulator unit 47 changes the inclination of the mirror 45. In this way, an irradiation position of the treatment laser beam can arbitrarily be adjusted finely. Fine adjustment of the irradiation position can be made by not only movement of the mirror 45 but also movements of a zooming optical system 51 and the lens 41 of the illumination section 11. A protective filter 66 serves to block off a part of reflection light of the laser beams to protect operator's eye(s) OE during laser irradiation to the patient's eye PE. The filter 66 is movable into or out of the observation optical path as indicated by an arrow in FIG. 2, so that it is disposed out of the optical path during observation.

The laser delivery optical system 12 is arranged to change a spot size of the laser beam (the treatment laser beam and the aiming beam) emitted from the main box 5 and delivers the laser beam to the patient's eye PE. The one end of the fiber 30 is formed with a fiber end 31 from which the laser beam emerges. The laser beam emerging from the fiber end 31 is changed in spot size (spot diameter and irradiation area) by the zooming optical system 51 constituted of various kinds of lenses. The spot size can be adjusted in a range of 50 μm (the diameter of the fiber end 31 in the present embodiment) to 1000 μm. Changing the spot size can be achieved by adjustment of the positions of the lenses. The laser beam with the changed spot size by the zooming optical system 51 is delivered to the illumination section 11 by the mirror 52. The laser beam is then coaxially combined with the illumination light by the mirror 45.

The observation optical system internally installed in the microscope 20 includes an objective lens 61 used in common between the right and left observation optical paths, a rotating drum 70 housing an optical system (the details thereof will be described later), an image forming lens 62, an erect prism 63, a field stop 64, and eyepieces 65, which are arranged in each of the right and left optical paths. The rotating drum 70 constituting a mechanism 75 is configured to mount plural pairs of optical elements arranged at intervals of about 60°. In the present embodiment, three switchable optical paths are provided. On one of the three optical paths, a pair of variable magnification lenses 71a and 71b as a variable magnification optical system 71 for changing the observation magnification is placed. On another optical path, openings 73 with no lens are arranged. On the remaining optical path, a pair of prisms 72a and 72b as a viewing angle changing optical system 72 for changing an observation viewing angle is placed. The above pairs of optical elements are arranged on each of the right and left optical paths. The variable magnification lenses 71a and 71b are disposed in diametrically opposite positions in the rotating drum 70. Similarly, the prisms 72a and 72b are disposed in diametrically opposite positions different from those of the lenses 71a and 71b in the rotating drum 70. In FIG. 2, the rotating drum 70 has three switchable optical paths but may have more optical paths to add another variable magnification optical system for different magnification from the variable magnification optical system 71. The switchable paths of the rotating drum 70 include at least three types.

Figure 3:
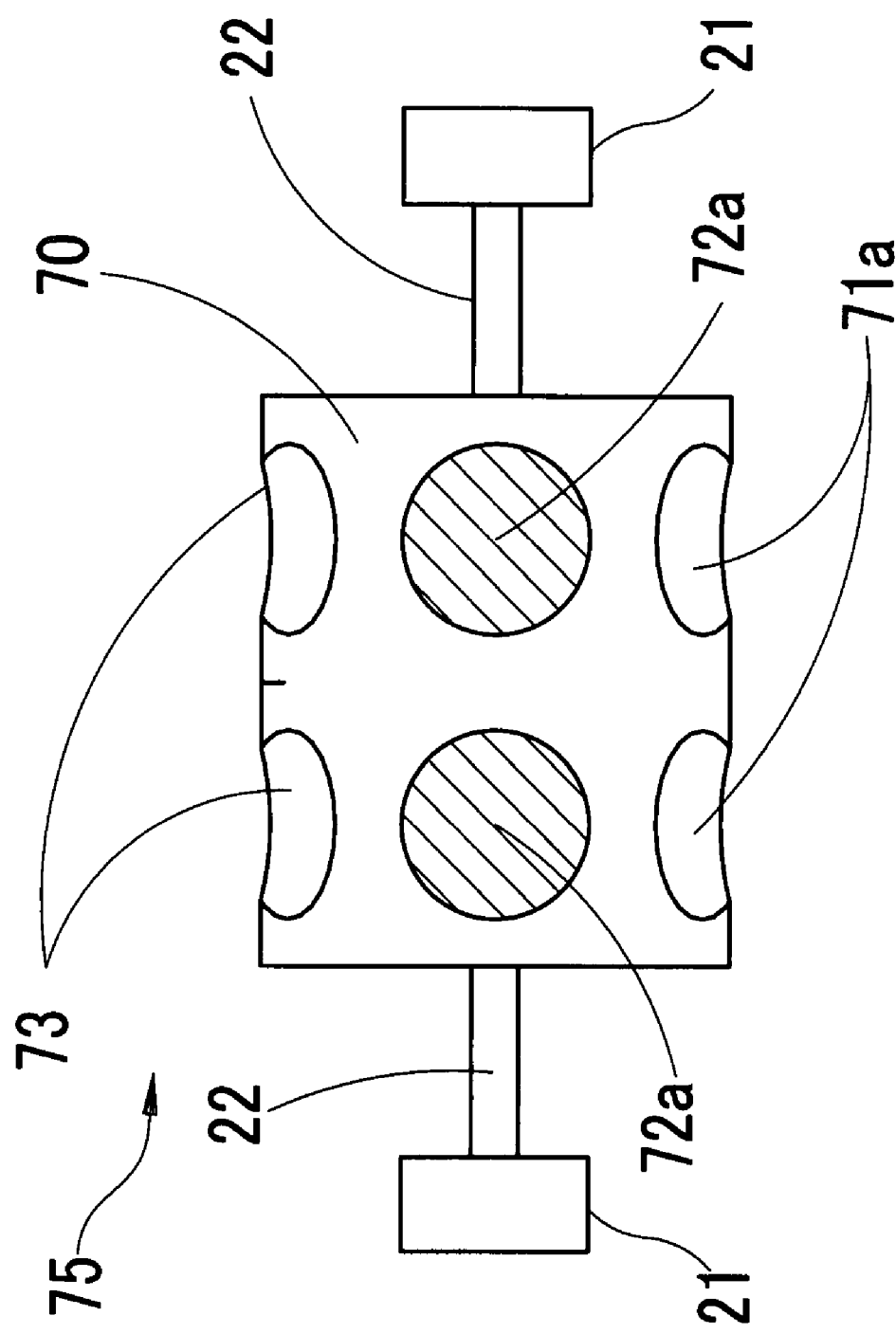
FIG. 3 is a front view of a mechanism including a rotating drum, seen from the side of an observer.

FIG. 3 is a front view of the mechanism 75 seen from the side of the observer. The rotating drum 70, provided with the openings 73 for each of a right eye and a left eye, the variable magnification optical system 71, and the viewing angle changing optical system 72, is connected with the knobs 21 on right and left sides through shafts 22. The shafts 22 are perpendicular to the observation optical axis for right and left eyes and serve as rotating shafts of the rotating drum 70 (the central axis of the rotating drum 70). Upon rotation of the knobs 21 by the operator, the rotating drum 70 is rotated about the shafts 22. The variable magnification optical system 71 and the viewing angle changing optical system 72 are selectively positioned on the observation optical axis (on the observation optical path) of each of the right and left eyes.

Switching of the observation magnification will be described below. As shown in FIG. 2, the observation magnification is switched according to insertion/removal of the variable magnification optical system 71 with respect to the optical axis of each of the right and left eyes. In the present embodiment, the observation magnification can be selected from 10-power, 16-power, and 25-power. FIGS. 4A and 4B are schematic diagrams of the optical systems of the microscope 20 seen from above, in which the protective filter 66 is not shown in the figure. In FIGS. 4A and 4B, R denotes an operator's right eye and L denotes an operator's left eye. As shown in FIG. 4A, when the openings 73 of the rotating drum 70 are disposed on the optical axes of the right and left eyes respectively, the optical axes of the right and left eyes are of no lenses. In this state, a combination of the powers of the eyepieces 65 and other lenses determines a comprehensive observation magnification, which is 16-power in the present embodiment. Next, a different case is explained, in which the rotating drum 70 is rotated to dispose the variable magnification optical system 71 on the optical axis of each of the right and left eyes. In FIG. 2, when the variable magnification optical system 71 is disposed on the optical axis, the observation magnification is switched from 16-power to 10-power or 25-power. This magnification switching is achieved because the variable magnification lenses 71a and 71b have different refractive powers and they are disposed in different positions from the positions for 16-power (i.e., in interchanged positions) when seen from the side of the eyepieces 65. The variable magnification lens 71a is larger in power than the variable magnification lens 71b. Accordingly, when the variable magnification lens 71b is placed on a near side and the variable magnification lens 71a is placed on a far side relative to the eyepieces 65 (as shown in FIG. 2), the observation magnification becomes 25-power. Reversely, when the variable magnification lens 71a is disposed on a near side and the variable magnification lens 71b is disposed on a far side relative to the eyepiece 65, the observation magnification becomes 10-power.

Switching of the observation viewing angle is explained below. FIG. 4B is a diagram showing a state where the viewing angle changing optical systems 72 are aligned with the optical axes of the right and left eyes respectively by rotation of the rotating drum 70. The observation viewing angle in FIG. 4A is assumed to be θ1 as a reference viewing angle. And an observation viewing angle in FIG. 4B is assumed to be θ2.

As shown in FIGS. 4A and 4B, the observation viewing angle is switched by insertion/removal of the viewing angle changing optical systems 72 into/from the optical axes. The prisms 72a and 72b are components whereby the optical axis of light passing through them is deflected. In the present embodiment, the prisms 72a and 72b are made of the same material and in the same size, but they are placed with the base directions thereof facing opposite to each other and also symmetric relative to the optical axes of the right and left eyes. This placement of the prisms 72a and 72b allows the degree of deflection of the optical axis to be adjusted.

The case where the prisms 72b and 72a are arranged in this order on the optical axis from the side of the eyepieces 65 as shown in FIG. 4B is explained. In this state, the optical axes of the right and left eyes are deflected inward (toward the optical center of the objective lens 61). In FIG. 4B, the distance between the optical axes of the right and left eyes is narrowed than that in FIG. 4 by effect of the prisms 72b and 72a. Accordingly, the observation viewing angle θ2 becomes smaller than the observation angle θ1.

Figure 4C:
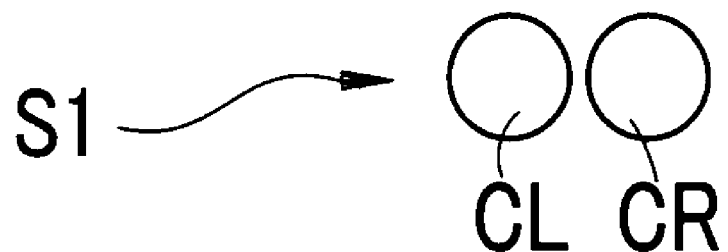
FIGS. 4C and 4D are diagrams showing states of binocular vision in relation to the observation viewing angles of FIGS. 4A and 4B.
Figure 4D:
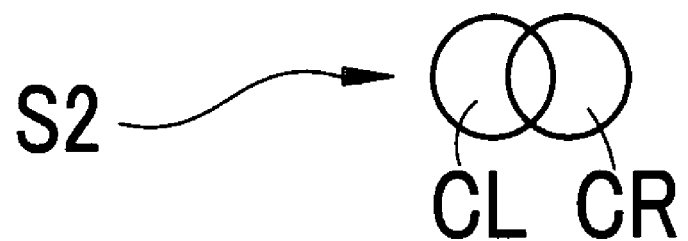

FIG. 4C schematically shows a state S1 of binocular vision for the observation angle θ1. FIG. 4D schematically shows a state S2 of binocular vision for the observation angle θ2. In the states S1 and S2, circles CR and CL schematically show a right field of view and a left field of view respectively. As the circles CR and CL come close to each other, the degree of stereoscopic vision (binocular vision) decreases. In the state S2, the right and left field of views come closer to each other as compared with in the state S1. Accordingly, an overlapping area of the circles CR and CL increases. The degree of stereoscopic vision of the observer in the state S2 is inferior to that in the state S1. However, the observation viewing angle θ2 is smaller than the observation viewing angle θ1. Even where the lateral width of iris of the patient's eye is small, which is likely to cause eclipse of the optical axis of either the right or left eye in the case of angle θ1, the change to the angle θ2 allows binocular observation of the fundus F in a stereoscopic vision. The eclipse of the optical axis tends to be caused when a peripheral portion of the fundus of the patient's eye PE is observed. When the patient's eye PE moves to the right or left, the optical axis of either one of the right and left eyes is likely to be eclipsed by the iris in the case of angle θ1.

To increase the viewing angle more than the viewing angle θ1, the placement of each pair of prisms 72a and 72b shown in FIG. 4B has only to be reversed. When the rotating drum 70 is rotated 180° by the knobs 21, the prisms 72a and 72b are reversely placed, thus increasing the viewing angle. The increased viewing angle in this way can provide clear stereoscopic vision. This is also advantageous in the case where the patient's eye PE has a wide pupil or during observation and treatment of an anterior segment which needs no careful attention to eclipse of the right and left observation optical axes.

An operation of the ophthalmic laser treatment apparatus 100 having the above configuration will be explained below. The operator first instructs the patient to place his head on the headrest 6 to fix the position of the patient's eye PE. The operator selects an amount of illumination light and other conditions by operating the switches on the main box 5. Successively, the operator puts the contact lens CL and others on the anterior segment of the patient's eye PE and observes the eye PE through the eyepieces 65. To change the observation magnification, the operator has to rotate the knob 21, thereby selectively inserting/removing the openings 73, the pair of variable magnification optical system 71, and others into/from the optical axes to switch the magnification to a suitable one for the area of an affected part to be observed.

The following explanation is made on an operation for treatment of the patient's eye PE by irradiation of the affected part with the laser beam. For example, the photocoagulation treatment of the fundus of the eye PE will be explained. When the peripheral portion of the fundus is to be photocoagulated, there may be a case where the field of view at the viewing angle θ1 as shown in FIG. 4A is eclipsed by the iris, which precludes binocular observation of the fundus of the eye PE. In such a state, it is undesirable for the operator to perform the photocoagulation treatment while observing the fundus with one eye. This is because the operator cannot sufficiently obtain a sense of depth of the fundus for lack of stereoscopic vision caused by the monocular observation. In particular, in the case where a retina is separated from the fundus resulting from retinal detachment, edema, and the like, it is more difficult for the operator to sufficiently obtain the sense of depth. Thus, the operator switches the viewing angle to a smaller viewing angle θ2 by operation of the knob 21 and then performs irradiation of the laser beam to the affected part under binocular observation.

After the observation of the fundus, the operator operates the switches arranged on the main box 5 to set an amount of energy, an irradiation time, and other conditions of the laser beam to be irradiated to the affected part. Further, the operator operates a knob and the like provided in the zooming optical system 51 to set the spot size of the laser beam. While observing the patient's eye PE, the operator then makes alignment of the position of laser irradiation by operating the joystick 4. And then the operator irradiates the laser beam to the affected part by pressing a footswitch (not shown).

In the above manner, the observation and treatment of the patient's eye PE are performed. During this process, the operator conducts the treatment while supporting the contact lens CL on the eye PE with hand. Accordingly, when the working distance from the eyepieces 65 to the patient's eye PE is shorter, it is easier for the operator to fix the contact lens CL on the eye PE. In Patent document 2, the unit for changing observation magnification and the unit for changing observation viewing angle are placed in different positions on the optical axis. In the present embodiment, on the other hand, the optical elements used for changing the observation magnification and the observation viewing angle are mounted in the rotating drum 70. The variable magnification optical system 71 and the viewing angle changing optical system 72 are switched in the predetermined positions on the optical axis (in the present embodiment, the location of the rotating drum 70) to change the variable magnification and the viewing angle respectively. It is therefore possible to change the observation magnification and the observation viewing angle without extending the working distance. As compared with Patent document 1, the slit lamp of the present embodiment can achieve switching of the observation magnification and the observation viewing angle by simply changing the positions of the optical elements mounted in the rotating drum 70. This needs no large change of the mechanism and thus provides an advantage in cost. When the observation magnification is to be changed after the observation viewing angle is changed, the powers of the eyepieces 65 have only to be changed. Furthermore, several kinds of contact lenses CL having different powers may be prepared for observation and treatment of the patient's eye PE so that an appropriate one is selected. For example, the contact lenses CL of 1-power, 1.3-power, 2-power, etc. are available.

The treatment using the tilting mechanism of the head section 80 will be explained below. The aforementioned explanation shows the configuration and operation for changing the observation viewing angle to avoid the affect of eclipse by the iris in relation to the treatment of the fundus of the patient's eye PE. However, a reduced observation viewing angle is likely to cause the prism mirror 55 to appear in the observation field of view (see FIG. 6E). To minimize such appearance of the mirror 55 in the observation field of view, the tilting operation of the head section 80 is performed.

Figure 5B:
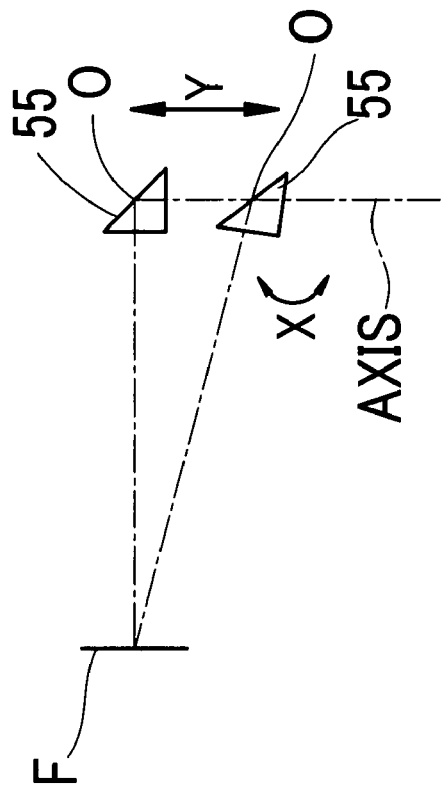
FIGS. 5A and 5B are schematic diagrams to explain a tilting mechanism of a head section.
Figure 5A:
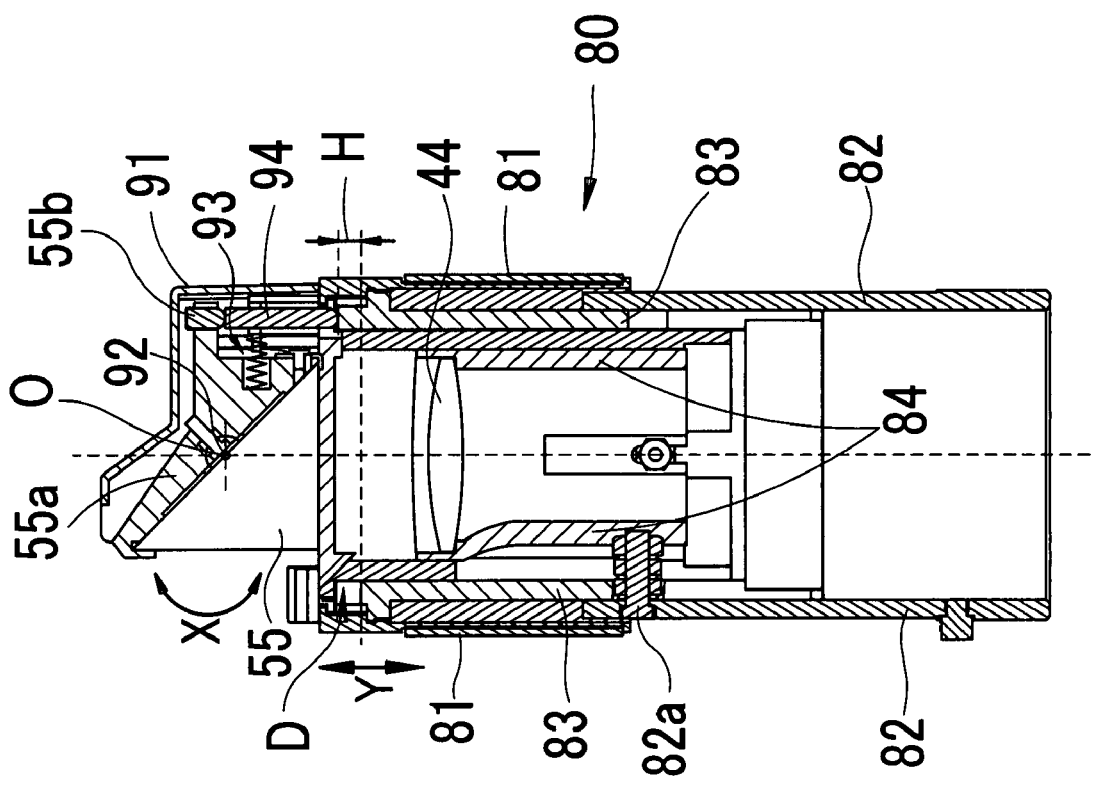

FIGS. 5A and 5B show the tilting mechanism of the head section 80; FIG. 5A is a sectional view of a main part of the head section 80. An inner sleeve 83 fixed to the inside of the first outer sleeve 81 can be rotated in association with the rotation of the outer sleeve 81. A pin 82a is fixed in an upper part of a second outer sleeve 82 mounted on a base 99. The pin 82a is engaged in a cam groove formed in the inner sleeve 83 and others, allowing the inner sleeve 83 to be rotated in association with the rotation of the first outer sleeve 81. The inner sleeve 83 is movable upward/downward through the pin 82a relative to the second outer sleeve 82.

A lens holder 84 in which a lens 44 is placed is fixed to the inside of the inner sleeve 83. Thus, the position of the lens 44 can be moved in the vertical direction in association with the vertical movement of the inner sleeve 83. A broken line (a rotating axis of the outer sleeve 81 and others) vertically extending in FIG. 5A coincides with the optical axes of the illumination light and the laser beams.

The mirror 55 is supported by a holder 55a to which an axial pin 92 is attached in such a manner as to be rotatable about a coordinate O. The holder 55a is further attached with an end member 55b. In a cover 91, a pin 94 is placed movable in the vertical direction. A lower end of the pin 94 is in contact with a slope D (mentioned later) and an upper end of the pin 94 is in contact with the end member 55b. A spring 93 is installed, in a compressed form, between the holder 55a and the pin 94. Accordingly, the holder 55a is urged clockwise about the coordinate O by the spring 93.

The tilting operation of the head section 80 having the above configuration will be explained below. The first outer sleeve 81 is first rotated by the operator. The inner sleeve 83 is formed, on its top, with the slope D having a height difference H. In association with the rotation of the outer sleeve 81, therefore, the height of the slope D contacting the lower end of the pin 94 varies. Thus, the pin 94 contacting with the slope D is moved upward or downward, changing its height. As the pin 94 is moved upward or downward, the holder 55a is rotated in a direction indicated by an arrow X in FIGS. 5A and 5B. Specifically, when the pin 94 is moved downward, the holder 55a is rotated clockwise about the coordinate O by the urging force of the spring 93. In addition, since the inner sleeve 83 is also rotated, the position of the head section 80 is moved upward or downward as indicated by an arrow Y in FIG. 5A. The lens holder 84 is moved simultaneously, changing the position of the lens 44. This allows a focus of the illumination light and the laser beams to be corrected.

FIG. 5B shows a shift of the optical axis caused by the tilting. The operator rotates the first outer sleeve 81 to move down the height of the head section 80. In association with this operation, the mirror 55 is simultaneously rotated (tilted) clockwise about the coordinate O. As shown in FIG. 5B, the upward or downward movement of the mirror 55 causes the optical axis to be shifted to a horizontal one or an elevated one (to look up at the fundus F). Accordingly, even when the height of the head section 80 in the vertical direction is changed, the image forming positions (an intersecting point of the optical axis with the fundus F) of the laser beams and the illumination light on the fundus F remain unchanged. In other words, the optical paths of the laser beams and the illumination light can be shifted without changing the image forming position on the fundus F.

Figure 6A:
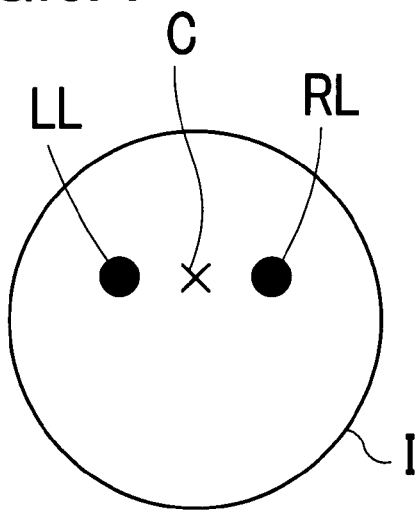
FIGS. 6A to 6C are diagrams to explain a relation between optical axes of right and left eyes and a laser optical axis.
Figure 6D:
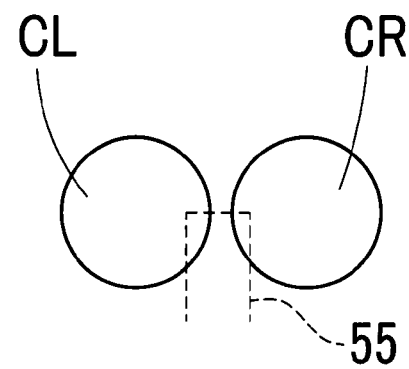
FIGS. 6D to 6F are diagrams to explain a relation between observation field of view and a prism mirror.
Figure 6B:
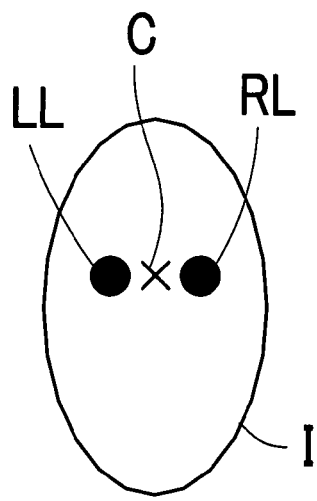
Figure 6E:
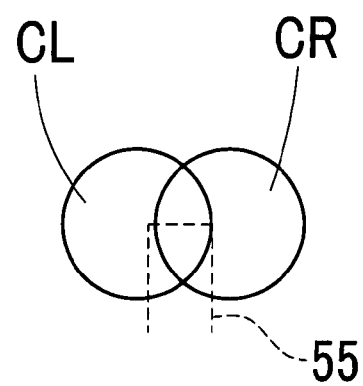
Figure 6C:
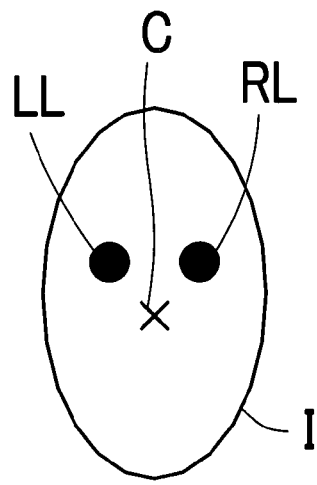
Figure 6F:
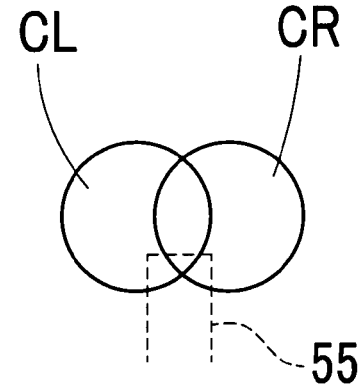

FIGS. 6A to 6C show a relation between the optical axes of the right and left eyes of the operator and the optical axis of the laser beam during laser irradiation. And FIGS. 6D to 6F show a relation between the observation field of view and the prism mirror 55. In FIGS. 6A to 6C, the observation optical axis RL of the right eye and the observation optical axis LL of the left eye are illustrated by black circles. And the laser optical axis C is illustrated by a mark "x". The laser optical axis C is the same as the illumination optical axis. A peripheral edge of the pupil I of the patient's eye PE is illustrated by a circular or elliptic line. In fact, the optical axes RL, LL and the laser optical axis C converge at one point on the eye fundus.

FIG. 6A shows a state where the patient's eye PE faces almost forward and the observation viewing angle remains unchanged (the state corresponding to the viewing angle θ1 as shown in FIG. 4A). In the state shown in FIG. 6A, the optical axes RL and LL of the right and left eyes are not eclipsed by the iris. Further, the laser optical axis C is positioned between the optical axes RL and LL of the right and left eyes. In this state, the image of the mirror 55 slightly enters in the edge portion of the observation field of views CL and CR as shown in FIG. 6D. However, the area of the image of the mirror 55 which may interfere with the field of views of the operator is small. Therefore, the operator can perform appropriate laser irradiation without interruption of observation by the mirror 55.

As shown in FIG. 6B, however, a problem may occur when the pupil I is observed as an elliptic shape. FIG. 6B schematically shows a state where the patient's eye PE moves to the right or left. Since the shape of the pupil I is vertically elongated elliptic, the observation viewing angle θ1 is switched to the observation viewing angle θ2 smaller than the angle θ1 to avoid the optical axes RL, LL of the right and left eyes from becoming eclipsed by the iris. In this state, the mirror 55 may largely appear in the observation field of views of the right and left eyes as shown in FIG. 6E. Accordingly, the laser optical axis C positioned between the optical axes RL and LL comes close to the optical axes RL and LL, leading to a difficulty in performing laser irradiation.

To reduce the above disadvantage, the aforementioned tilting of the head section 80 is performed. Specifically, the light projecting unit 10 is moved downward (see FIG. 1) to lower the height of the mirror 55.

FIGS. 6C and 6F schematically show a relation between the optical axis C and the mirror 55, etc. in a state after the tilting of the head section 80 is performed. As shown in FIG. 6C, the optical axis C is moved down by downward movement of the mirror 55. Accordingly, the mirror 55 less appears in the observation field of views of the right and left eyes, allowing the operator to easily perform laser irradiation.

As described above, the tilting operation of the head section 80 causes the mirror 55 to move downward and tilt. Thus, the interference with observation by the mirror 55 can be minimized even when the observation viewing angle is reduced. Accordingly, appropriate laser irradiation can be performed.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A binocular slit lamp microscope for stereoscopically observing a patient's eye, comprising:
    an illumination section for irradiating slit illumination light to the patient's eye;
    a binocular microscope section including an observation optical system, including:
        an objective lens;
        right and left eyepieces; and
        right and left erect prisms placed between the objective lens and the right and left eyepieces,
        the observation optical system being adapted to allow reflection light of the slit illumination light from the patient's eye to pass therethrough; and
    rotating drum rotatably placed in a predetermined position between the objective lens and the right and left erect prisms on right and left optical paths of the observation optical system;
    an observation magnification changing optical system for changing observation magnification, the observation magnification changing optical system being placed on the rotating drum and including right and left variable magnification lenses to be placed symmetrically on the right and left optical paths; and
    a binocular viewing angle changing optical system for changing a binocular viewing angle between right and left viewing paths, the binocular viewing angle changing optical system being placed on the rotating drum and including right and left deflecting members to be placed symmetrically on the right and left optical paths, and the deflecting members being configured to symmetrically deflect the reflection light having passed through each of the deflection members toward an optical center axis of the objective lens or reversely,
    the observation magnification changing optical system and the binocular viewing angle changing optical system being selectively placed on the right and left optical paths by rotation of the rotating drum.

2. The slit lamp microscope according to claim 1, wherein the right and left deflecting members are right and left prisms to be placed symmetrically on the right and left optical paths, the prisms having opposite base directions to each other.

3. An ophthalmic laser treatment apparatus comprising a treatment laser source and an irradiation optical system for irradiating a laser beam emitted from the laser source to the patient's eye,
    wherein the slit lamp microscope set forth in claim 1 is used as an observation unit for observing the patient's eye.

4. The ophthalmic laser treatment apparatus according to claim 3, wherein the slit lamp microscope comprises:
    a waveform combining mirror for combining waveforms of the laser beam and the slit illumination light of the illumination section;
    a mirror for reflecting the waveform-combined laser beam and illumination light toward the patient's eye; and
    a holder which holds the mirror, the holder being arranged to be movable vertically and simultaneously tiltable while keeping a portion of the patient's eye to which the laser beam and illumination light are irradiated.

* * * * *